United States Patent [19]

Trinklein

[11] Patent Number: 4,663,007
[45] Date of Patent: May 5, 1987

[54] METHOD TO EVALUATE SHEET METAL LUBRICANTS CRATERING POTENTIAL ON METAL PRIMER

[75] Inventor: Donald W. Trinklein, Rochester, Mich.

[73] Assignee: Chrysler Motors Corporation, Highland Park, Mich.

[21] Appl. No.: 791,234

[22] Filed: Oct. 25, 1985

[51] Int. Cl.$^4$ .............................................. C25D 13/00
[52] U.S. Cl. ............................. 204/180.2; 204/181.3; 204/181.7
[58] Field of Search .............. 204/180.2, 181.1, 181.3, 204/181.7

[56] References Cited

U.S. PATENT DOCUMENTS

| | | | |
|---|---|---|---|
| 3,502,511 | 3/1970 | Forsberg | 204/181.3 X |
| 4,292,096 | 9/1981 | Murakami et al. | 204/181.3 X |
| 4,311,535 | 1/1982 | Yasuhara et al. | 204/181.3 X |
| 4,321,305 | 3/1982 | Castellucci et al. | 204/181.3 X |
| 4,376,024 | 3/1983 | Anderson et al. | 204/180.2 |
| 4,419,199 | 12/1983 | Hauffe et al. | 204/181.3 |

*Primary Examiner*—T. Tung
*Attorney, Agent, or Firm*—Gerald P. Dundas

[57] ABSTRACT

A test procedure developed in our laboratory for determining the cratering potential of sheet metal lubricants on cathodic E-Coat primer. Lubricants trapped in flanges and other tight fitting areas are expelled onto the uncured E-Coated surfaces during the baking operation, causing craters to form. Surfaces containing craters must be refinished before application of the color coat or they detract from the vehicle's appearance.

9 Claims, 3 Drawing Figures

U.S. Patent  May 5, 1987  4,663,007
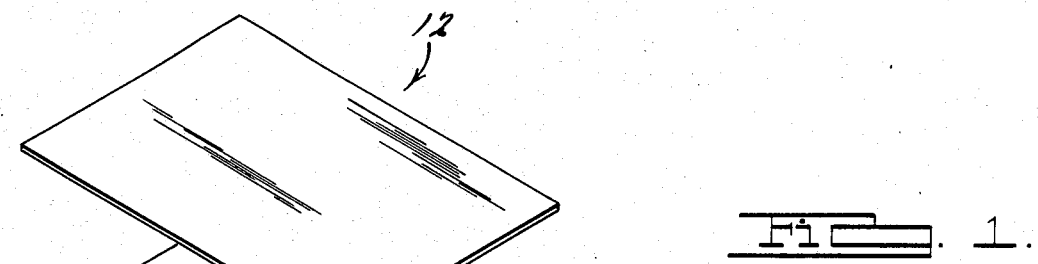
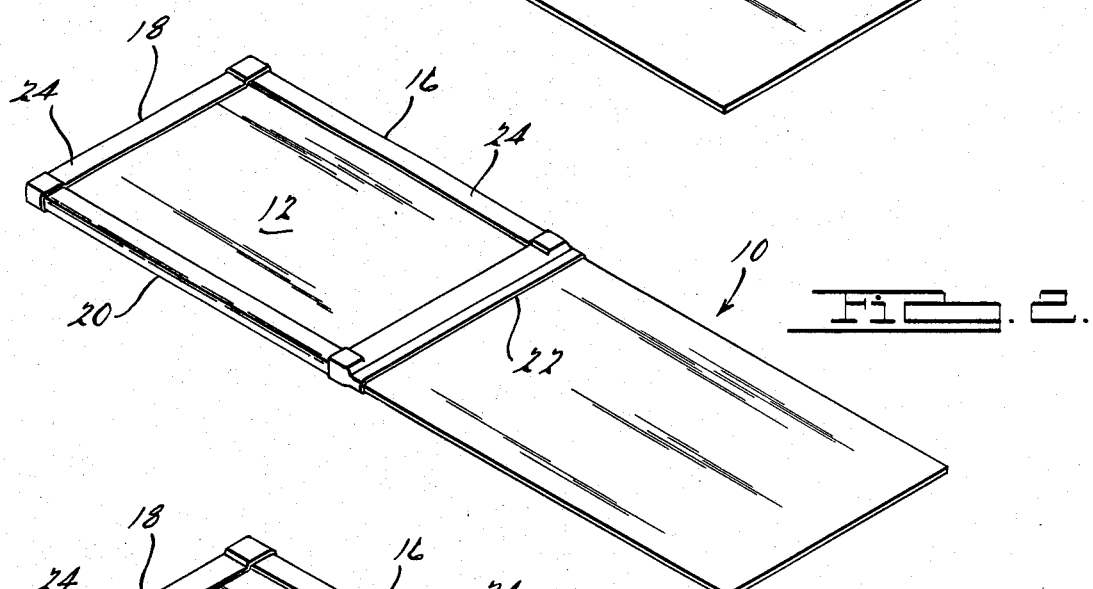
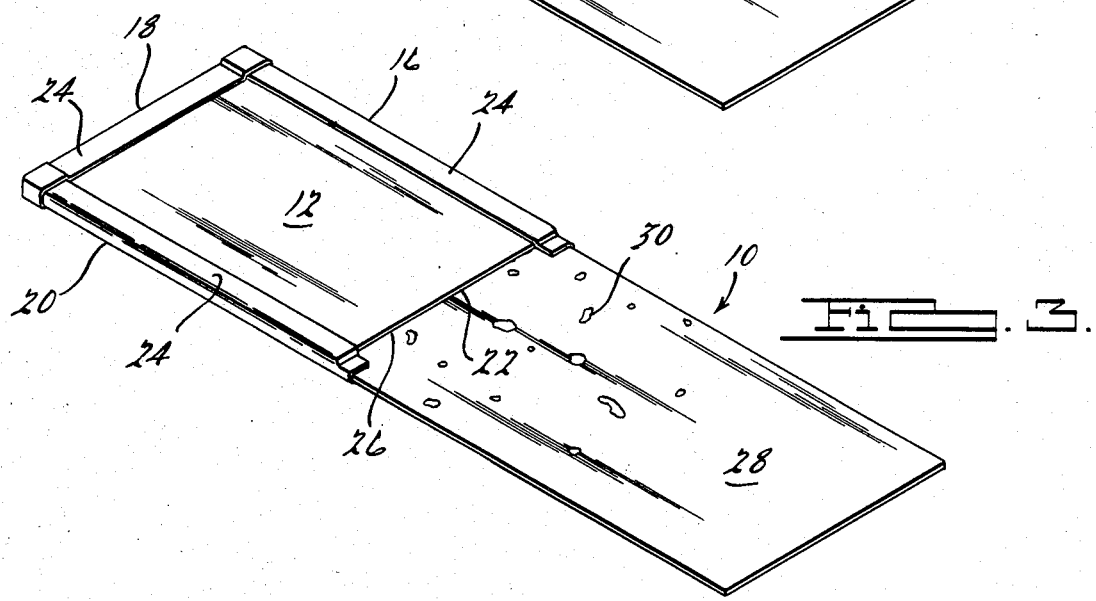

METHOD TO EVALUATE SHEET METAL LUBRICANTS CRATERING POTENTIAL ON METAL PRIMER

FIELD OF THE INVENTION

This invention generally relates to surface coatings and in particular to a test procedure for determining if certain compositions will cause imperfections such as surface pitting, generally termed "cratering" in the surface coatings. More specifically, the invention relates to a novel test procedure for identifying mill oils and drawing compounds which cause cratering.

BACKGROUND OF THE INVENTION

The use of electrophoretic primers has greatly increased in the automotive industry due to the superior coating obtained in many applications. This type of primer provides a highly uniform film thickness and is capable of reaching highly inaccessible areas which are difficult to coat by other painting processes. This increased usage, however, has also seen a rise in surface pitting or cratering in the electrophoretic primer coating which detracts from surface finish and often requires refinishing of the primer coating before application of a color coat.

In examining this cratering problem it has been determined that cratering principally occurs from four entirely different sources: (a) oil deposited on the phosphated steel prior to reaching the electrocoat tank; (b) oil floating on the top of an electrocoat bath; (c) oil emulsified into the electrocoat bath; and (d) oil on the coated surface of an uncured electrocoat film. The last source has been found to be a major source of crater problems and investigation has shown that oils and various metal working lubricants are frequently trapped in flanges and other tight fitting areas. These oils and lubricants were found to be expelled onto the uncured electrophoretic primer during the baking operation used to cure the primer causing craters to form.

Much attention is being given to cleaning and washing procedures to insure removal of such oil and lubricants before the metal is washed with primer but complete removal appears unobtainable as some material is frequently trapped in hem-flanges, etc. Accordingly, the metal working chemical art has turned attention to developing oils and metal working materials which have greater compatibility with uncured electrophoretic primers. Due to the many variations in metal and primer compositions, however, it was determined that a test procedure to identify the mill oils and drawing compounds which cause cratering in any given application would be highly desirable.

BACKGROUND ART

Efforts to develop a test procedure to evaluate sheet metal lubricant cratering potential on electrophoretic primers have taken different directions with the result that there is presently no uniform test procedure. Accordingly, prior to the development of the test procedure of this invention there was no standard test which would permit sharing of data between metal working chemical supplier companies and their customers. While one or two companies have their own test procedure for cratering potential, there is no well-defined published standard test procedure.

The test method of this invention establishes a repeatable step wise procedure. It is derived from research in the metal working elements industry which established that lubricants trapped in flanges or hem areas are frequently not washed out prior to the electrocoat process. When heat is applied as during baking of the primer, the lubricant boils out and fall on the uncured paint and frequently produces a crater.

SUMMARY OF THE INVENTION

Responsive to the absence of a standard test procedure, it is an object of this invention to provide an efficient, rapid, economical and reproducible test procedure to evaluate the crater effect of sheet metal working lubricants on uncured electrophoretic primers.

The test procedure includes the steps of placing a metal working lubricant compound between metal test panels, sealing the edges of the test panels, coating the test panels by dipping them in an electrophoretic primer, washing the panels, unsealing one edge of the test panels and heating the panels to cure the primer. During the heating step, any lubricant compound which may volatize is collected on an uncured primer coating surface and its cratering effect visually determined.

DESCRIPTION OF THE DRAWING

The features and advantages of the test procedure for determining cratering potential of certain metal working chemicals on electrophoretic primers will be more clearly understood from the following description taken in conjunction with the accompanying drawing in which like reference numerals designate similar or corresponding structure, members and elements and in which:

FIG. 1 is a perspective view of two spaced apart metal test panels the larger of which having deposited thereon three drops of water based drawing lubricant;

FIG. 2 is a perspective view of the two test panels shown in FIG. 1 which have been brought into contact with the drawing lubricant sandwiched therebetween and the edges of the panels masked; and FIG. 3 is a perspective view of the two test panels of FIG. 2 after the unmasking of one edge portion and heating of the panels to permit the volatized drawing lubricant to escape from between the panels and deposit on another portion of the test panels.

DESCRIPTION OF THE TWO PREFERRED EMBODIMENTS

Referring now to the drawing, and in particular to FIG. 1, the test method for identifying metal working compounds which cause cratering in uncured electrophoretic primers utilizes two phosphated cold rolled test panels. In practice, good results have been achieved with a 4"×12" first panel 10 and an overlying 1¼"×12" second panel 12. The test panels were of prephosphated cold rolled material and should be cleaned with naphtha and petroleum ether to remove any surface contamination.

A small quantity of the metal working compound 14 to be evaluated for its cratering effect is placed on the surface of the first test panel 10 and the smaller second test panel 12 is then placed on the first test panel 10 so as to overlie the metal working compound 14. The quantity of metal working compound used in the test is not material and good results have been achieved with about 0.15 milliliter of the recommended aqueous dilution of the compound being tested. This amount generally represents three drops of the recommended strength metal working compound, the drops being applied to the first panel 10 by a dropping pipette or medicine dropper. Care should be used in placing the second panel on the first to avoid squeezing of the compound being evacuated from between the panels 10, 12.

The four edges 16, 18, 20 and 22 between the first and second panels 10, 12 are sealed by any suitable means. In practice, good results are achieved with one inch plating tape 24, such as shown in FIGS. 2 and 3. The sealed test panel sandwich is then placed into an agitated tank containing the electrophoretic primer and 250 volts and a maximum of 1 amp for 3 minutes is then applied to deposit a uniform electrophoretic primer layer on the test panels of approximately 0.0012 inch thickness. The coated test panel sandwich is then removed from the primer bath, rinsed with water to remove excess primer and stored in a vertical position for about 5 minutes to facilitate drainage of water and to allow the primer to set.

The tape from edge 22 is next removed from the panel sandwich to expose the gap 26 at the interface of the two panels 10 and 12 (FIG. 3) and the panel sandwich is heated to effect curing of the electrophoretic primer. In practice, it has been found desirable to have a gap between the panels of abut 0.002 inch. If the gap is much larger then the volatized compound is not expelled with any velocity from between the panels. This heating (350° F. for approximately 20 minutes for automotive electrophoretic primer) results in residual metal working compound 14 being vaporized, with the vapors exiting from between the panels 10, 12 through the unsealed gap 26 and redepositing on the outer surface 28 of the first test panel 10. This depositing of the metal working compound 14 vapors occurs before the primer on the panel outer surface 28 cures, and the formation of craters 30, if any, can be determined by visual inspection.

The critical steps of this test procedure are the sealing of the edges or gaps 16, 18, 20 and 22 between the test panels, and the careful heating of the test panel sandwich. These steps are necessary to insure that the vaporized metal working compound carries onto the surface 28 of the first test panel. Removing only edge tape 22 while leaving the other edges 16, 28 and 20 taped provides but a single path for the vaporized metal working compound to exit from the interior of the sandwich and insures that the vapors travel onto the first panel portion 28. Likewise, it has been found that air currents within the heating oven frequently blow the metal working compound vapor away from the uncured primer on portion 28 of the panel 10. Accordingly, it is desirable to shield the test panel sandwich as by placing the test panel sandwich in a box during the oven heating stage.

Another factor to consider is that the metal working compound vapors should deposit on the primer before complete cure of the primer, as this is the cause of the problem in the plant. Thus, it may be desirable in some situations to support the sandwich portion of the test panels on a heat sink, such as an aluminum block, to insure that the working compound volatizes prior to complete cure of the primer.

While the present invention has been disclosed in connection with the preferred embodiment thereof, it should be understood that there may be other embodiments which fall within the spirit and scope of the invention and that the invention is susceptible to modification and variation without department from the scope and fair meaning of the following claims.

What is claimed is:

1. A method for identifying drawing compounds which cause cratering in uncured cathodic electrocoat primers, said method comprising the steps of:
    (a) placing the drawing compound to be evaluated on a first test panel;
    (b) placing a second test panel on top of the first test panel and in contact with the drawing compound, said second test panel being positioned to overlie only a portion of said first test panel;
    (c) sealing the junctures of the two test panels;
    (d) electro-painting the test panels with a cathodic electrocoat primer and washing the panels to remove excess primer;
    (e) unsealing one juncture between the two panels to permit the drawing compound when heated to escape from between the two panels and deposit upon the first panel;
    (f) heating the test panels to cure the electrocoat primer; and
    (g) controlling said heating to cause the drawing compound to be expelled from between the test panels and deposited upon the first test panel prior to curing of the electrocoat primer on said first panel.

2. The method of claim 1 wherein the test panels are phosphated steel panels, said panels being of approximately the same width and thickness and said first panel having a greater length than the other to provide the surface upon which the drawing compound deposits when heated.

3. The method of claim 2 wherein approximately three drops of drawing compound spaced about one inch from each other are placed on the test panel.

4. The method of claim 1 wherein the junctures between the test panels are sealed with tape.

5. The method of claim 1 wherein the test panels are coated with said cathodic electrocoat primer by immersing the test panels in a primer bath.

6. The method of claim 1 wherein the electrocoat paint is cured by heating the test panels in a manner such that there is a minimum of air movement over the surface of the panels.

7. The method of claim 6 wherein the panels are placed in a box which is then heated in an oven to effect curing of the electrocoat paint.

8. The method of claim 1 wherein the panels are heated in an oven with the overlying portion of the two superimposed panels being supported on a heat sink to cause the drawing compound to volatize prior to curing of the outer surface of the primer.

9. A method for identifying drawing compounds which cause cratering in uncured cathodic electrocoat primer, said method comprising the steps of:
    (a) placing at least about 0.15 milliliter of an aqueous emulsion of the drawing compound to be evaluated on the surface of a first phosphated steel panel;
    (b) placing a second phosphated steel panel on said first panel so as to encapsulate said drawing compound between said panels;
    (c) sealing the juncture of said panels;
    (d) immersing said panels in a bath of cathodic electrocoat primer, removing the panels from the bath and washing said panels to remove excess primer.
    (e) unsealing a juncture of the panels to permit the drawing compound when heated to migrate from between the two panels and deposit upon a surface of the first panel extending beyond the second panel; and (f) heating the test panels to expel the drawing compound from between the panels, the panels during said heating being shielded from air movement which would interfere with the depositing of the expulsion, and said heating being controlled so that said expulsion occurs prior to curing of the cathodic electrocoat primer.

* * * * *